US008586087B2

(12) United States Patent  
Lee et al.

(10) Patent No.: US 8,586,087 B2
(45) Date of Patent: Nov. 19, 2013

(54) TEMPERATURE AND PH-SENSITIVE BLOCK COPOLYMER HAVING EXCELLENT GEL STRENGTH

(75) Inventors: Doo Sung Lee, Gyeonggi-do (KR); Kasala Dayananda, Gyeonggi-do (KR); Bong Sup Kim, Gyeonggi-do (KR)

(73) Assignee: Sungkyunkwan University Foundation for Corporate Collaboration, Gyeonggi-Do (KR)

( * ) Notice: Subject to any disclaimer, the term of this patent is extended or adjusted under 35 U.S.C. 154(b) by 1295 days.

(21) Appl. No.: 12/061,322

(22) Filed: Apr. 2, 2008

(65) Prior Publication Data

US 2008/0274190 A1 Nov. 6, 2008

(30) Foreign Application Priority Data

May 3, 2007 (KR) .................. 10-2007-0043190

(51) Int. Cl.
*A61K 9/00* (2006.01)
(52) U.S. Cl.
USPC .......... 424/487; 424/486; 514/2; 514/3; 514/8
(58) Field of Classification Search
USPC .......... 525/242, 123; 424/485, 425, 426, 424, 424/501, 491, 497, 486, 469, 487; 514/2, 3, 514/8, 12
See application file for complete search history.

(56) References Cited

U.S. PATENT DOCUMENTS 4,423,099 A * 12/1983 Mueller et al. .............. 428/35.2
4,963,638 A * 10/1990 Pazos et al. .................. 528/65

(Continued)

FOREIGN PATENT DOCUMENTS

JP 63-146812 6/1988
JP 01-131228 5/1989

(Continued)

OTHER PUBLICATIONS

Jeong B. et al., "Biodegradable Block Copolymers as Injectable Drug-Delivery Systems", Nature, Nature Publishing Group, London, vol. 388, No. 6645, Aug. 28, 1997, pp. 860-862.

*Primary Examiner* — James J Seidleck
*Assistant Examiner* — S. Camilla Pourbohloul
(74) *Attorney, Agent, or Firm* — Rabin & Berdo, P.C.

(57) ABSTRACT

An amphiphilic pentablock copolymer that is temperature- and pH-sensitive and has superior and sustained gel strength, includes (a) a hydrophilic triblock copolymer that is temperature-sensitive and that is a copolymer of a poly(ethylene glycol)-based compound and a biodegradable polymer that is one or more polymer selected from the group consisting of polylactide, polyglycolide, polycaprolactone, poly(caprolactone-lactide) random copolymer, poly(caprolactone-glycolide) random copolymer, poly(lactide-glycolide) random copolymer, and mixtures thereof; coupled with (b) a polyurethane-based oligomer (PU) that is pH sensitive and that includes a diisocyanate compound represented by a Formula as follows: $OCN-(CH_2)_n-NCO$, where n is an integer of 4 to 10, polymerized with a diol compound having a tertiary amine on a main chain thereof that is one or more of 1,3-bis{1-(2-hydroxyethyl) -4-pyridyl}propane and 1,4-bis(2-hydroxyethyl)piperazine, and is represented by Formulae as follows:

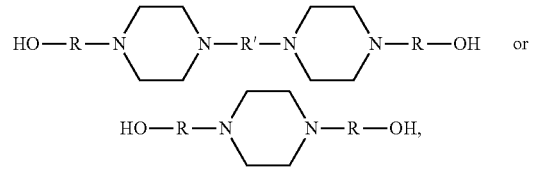

where R and R' are alkyl groups of 1 to 8 carbon atoms, respectively.

12 Claims, 5 Drawing Sheets

(56) References Cited

U.S. PATENT DOCUMENTS

| | | | |
|---|---|---|---|
| 6,201,065 B1 * | 3/2001 | Pathak et al. | 525/90 |
| 2003/0099709 A1 * | 5/2003 | Shah et al. | 424/469 |
| 2003/0147958 A1 | 8/2003 | Ahn et al. | |
| 2005/0019303 A1 | 1/2005 | Tsai et al. | |
| 2005/0176893 A1 | 8/2005 | Rana et al. | |
| 2006/0287710 A1 * | 12/2006 | Lendlein et al. | 623/1.19 |

FOREIGN PATENT DOCUMENTS

| | | |
|---|---|---|
| JP | 11-035655 A | 2/1999 |
| KR | 2000-0000603 | 1/2000 |
| KR | 2002-0030892 | 4/2002 |
| KR | 2007-0059101 | 6/2007 |
| WO | WO-99/07343 A1 | 2/1999 |
| WO | WO-2004-009664 A2 | 1/2004 |

* cited by examiner

TEMPERATURE AND PH-SENSITIVE BLOCK COPOLYMER HAVING EXCELLENT GEL STRENGTH

BACKGROUND OF THE INVENTION

1. Field of the Invention

The present invention relates to a temperature and pH-sensitive block copolymer, a method of preparing the block copolymer and a drug delivery using the block copolymer, and more particularly, to a multiblock copolymer, which has excellent gel strength and is sensitive to pH as well as temperature, a method of preparing the multiblock copolymer and a drug delivery system using the multiblock copolymer.

2. Description of the Related Art

Biocompatible polymers are used in various medical treatments, such as diagnosis and therapy, and are used as part of the human body. Recently, drug delivery systems that control a sol-gel transition phenomenon by changing the structure of molecules using biodegradable polymers or amphiphilic polymers, having both hydrophobic groups and hydrophilic groups, or by forming hydrogels using block copolymers, have been actively researched.

It is disclosed in U.S. Pat. No. 4,942,035 that the problem in which poly(ethylene glycol) and a poly(ethylene oxide)-poly(propylene oxide)-poly(ethylene oxide) block copolymer are not degraded in the body is improved using a copolymer of poly(alkylene glycol), which is a hydrophilic polymer, polylactide or polyglycolide, which is a biodegradable polyester polymer, and polycaprolactone.

Further, U.S. Pat. No. 5,476,909 discloses an A-B-A type triblock copolymer, which is a biodegradable polyester polymer, wherein the hydrophobic block (A) is limited to polylactide (PLA), polyglycolide (PGA) and copolymers thereof, and the hydrophilic block (B) is also limited to poly(ethylene glycol) (PEG) and derivatives thereof.

Further, U.S. Pat. No. 6,004,573 discloses an amphiphilic block copolymer, which is a biodegradable low molecular weight triblock copolymer comprising a hydrophobic block composed of a copolymer of PLA and PGA and a hydrophilic block composed of PEG. Due to the increase in the amount of the hydrophobic portion thereof, the copolymer remains in a sol state, which is a clear liquid state, at a temperature of 5° C. to 25° C., and is then automatically changed into a gel phase, that is, a water-containing semi-solid hydrogel phase, by the body temperature (37° C.) when it is put into the body. Therefore, the copolymer continuously remains in a gel phase and exhibits insolubility, and thermal gelation is induced reversibly, and thus the copolymer can be used as a drug delivery system for slowly discharging a drug present in a gel.

Further, U.S. Patent Application Publication No. 2006-0239961 discloses a water soluble, nonpeptidic polymer comprising two or more alkylene oxide-based oligomers linked together by hydrolytically degradable linkages such as ester linkage. Here, the polymer is an amphiphilic triblock copolymer having a central propylene oxide block or a butylene oxide block positioned between two ethylene oxide blocks. The polymer can be hydrolytically degraded into oligomers under physiological conditions. In aqueous media, the polymer preferably forms thermally reversible, hydrolytically degradable hydrogels that can be used, for example, for drug delivery and related biomedical applications.

However, since such block copolymers have sol-gel transition characteristics sensitive only to temperature, there are problems in that the temperature of an injection needle is the same as that of the body while they are injected into the body, so that the block copolymers are gelated before they are completely injected into the body, thereby clogging the injection needle.

Further, the above technologies are problematic in that the gel strength of the hydrogel is not sufficient even when a drug-containing hydrogel is completely injected into the human body, and a drug is excessively discharged due to the biodegradation of the hydrogel at the early stage of the injection of the drug, and thus the discharge of the drug cannot be controlled for a long time.

In addition, although it has been reported that block copolymers having a hydrophobic block including PLA, PGA, polycaprolactone (PCL) or the like are sensitive to pH, in reality, they are not suitable for practical use because they are not sensitive enough for use at the pH of the body.

Meanwhile, Korean Unexamined Patent Publication No. 2000-0012970 discloses a pH sensitive polymer comprising a sulfonamide group and a method of preparing the same. Here, in the case of a block copolymer hydrogel formed by random-copolymerizing sulfonamide monomers with dimethylacrylamide or isopropylacrylamide, since the pH sensitive component of the block copolymer hydrogel has anionic charges, the block copolymer hydrogel is largely used as a drug delivery system for delivering drugs having cationic charges, the use of which is limited.

Further, Korean Registered Patent No. 665672 discloses a method of preparing a block copolymer hydrogel using poly(β-amino ester) as a pH sensitive component. It is disclosed in this document that a block copolymer sensitive to pH as well as temperature is synthesized, and the synthesized block copolymer is gelated at a pH ranging from 7.0 to 7.4, which is similar to that in the body, and is solated outside the pH range, so that an injection needle is not clogged at the time of injecting the block copolymer into the body, whereas the injection needle is clogged at the time of injecting the conventional temperature-sensitive hydrogel thereinto, thereby safely forming gel in the body. Therefore, it can be seen that the prepared block copolymer can be used as a drug delivery system for discharging drugs targeted at specific temperature and pH.

However, the hydrogel is problematic in that, since its main chain has an ester bond and an amide bond, the gel strength thereof is rapidly decreased at the time of injection of the hydrogel into the body, and thus the use of the hydrogel as a drug delivery system for discharging drugs for a long time is limited.

SUMMARY OF THE INVENTION

Accordingly, the present invention has been made keeping in mind the above problems occurring in the prior art, and an object of the present invention is to provide a novel amphiphilic block copolymer, which has excellent gel strength and is sensitive to pH as well as temperature, by synthesizing a polyurethane-based oligomer, which is a component exhibiting ionization characteristics because it is sensitive to the pH in the body, and then coupling the oligomer with a temperature-sensitive block copolymer, which is composed of a biodegradable polymer, and a method of preparing the block copolymer.

Another object of the present invention is to provide a hydrogel type drug delivery system comprising physiologically active substances which can be included in the block copolymer.

A further object of the present invention is to provide a temperature and pH-sensitive block copolymer having excellent gel strength, which can be usefully utilized by suitably changing the constituents, molar ratio, molecular weight and/or functional groups of the block copolymer, and thus designing the block copolymer to have target aiming properties in cancer cells, genetic variations and other applications, a method of preparing the block copolymer, and a drug delivery system using the block copolymer.

A still further object of the present invention is to provide a temperature and pH-sensitive block copolymer having excellent gel strength, which can prevent the initial burst release of a drug and can release the drug for a long time, a method of preparing the block copolymer, and a drug delivery system using the block copolymer.

In order to accomplish the above objects, the present invention provides a temperature and pH-sensitive block copolymer having excellent gel strength, comprising: (a) a poly(ethylene glycol)-based compound (A) or a copolymer (B) of the poly(ethylene glycol)-based compound (A) and a biodegradable polymer; and (b) a polyurethane-based oligomer (C).

In the present invention, the oligomer (C) is coupled with the poly(ethylene glycol)-based compound (A) or the copolymer (B).

Further, the poly(ethylene glycol)-based compound is represented by Formula below:

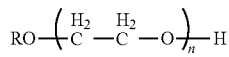

wherein R is hydrogen or an alkyl group of 1 to 5 carbon atoms, and n is a natural number ranging from 11 to 45.

Further, the poly(ethylene glycol)-based compound has a number average molecular weight ranging from 1000 to 5000 g/mol.

Further, when the poly(ethylene glycol)-based compound is poly(ethylene glycol) (PEG), the poly(ethylene glycol) (PEG) has a number average molecular weight ranging from 1000 to 2000 g/mol.

Further, the biodegradable polymer is biodegradable aliphatic polyester.

Further, the biodegradable polymer is one or more selected from the group consisting of polylactide (PLA), polyglycolide (PGA), polycaprolactone (PCL), poly(caprolactone-lactide) random copolymer (PCLA), poly(caprolactone-glycolide) random copolymer (PCGA), poly(lactide-glycolide) random copolymer, and mixtures thereof.

Further, the molecular weight ratio of the poly(ethylene glycol)-based compound to the biodegradable polymer is in the range of 1:1 to 1:3.

Further the polyurethane-based oligomer is formed by polymerizing a diisocyanate compound with a diol compound.

Further, the diisocyanate is represented by Formula below:

OCN—(CH$_2$)$_n$—NCO wherein n is an integer of 4 to 10.

Further, the diisocyanate is one or more selected from the group consisting of 1,2-diisocyanate ethane, 1,4-diisocyanate butane, 1,3-diisocyanate butane, 1,6-diisocyanate hexane, 1,7-diisocyanate heptane, 1,8-diisocyanate octane, 1,9-diisocyanate nonane, 1,10-diisocyanate decane, 1,12-diisocyanate decane, bis(4-isocyanatecycloethyl)methane, bis(4-isocyanatephenyl)methane, bis(4-isocyanatephenyl)ether, bis(4-isocyanatephenyl)sulfone, 4,4'-diphenylmethane diisocyanate, and hydrogenated 4,4'-diphenylmethane diisocyanate.

Further, the diol compound, comprising tertiary amine on a main chain thereof, is represented by Formulae below:

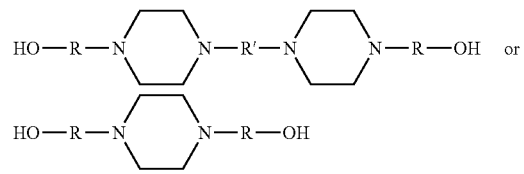

wherein R and R' are alkyl groups of 1 to 8 carbon atoms, respectively.

Further, the diol compound is one or more selected from the group consisting of 1,3-bis{1-(2-hydroxyethyl)-4-peridyl}propane, 1,4-bis(2-hydroxyethyl)piperazine, 1,4-bis(2-hydroxymethylphenyl)piperazine, and 1,4-bis-(2-hydroxyfluorophenyl)piperazine, 1,4-bis(2-hydroxyethyl)piperazine mono-lactate, 1,4-bis(2-hydroxyethyl)piperazine di-lactate, 1,3-[1-2-hydroxyehtyl)-4-piperidyl]propane mono-lactate, 1,3-[1-(2-hydroxyehtyl)-4-piperidyl]propane di-lactate.

Further, the molar ratio of the diisocyanate to the diol in reaction is in the range of 1:1 to 1:3.

Further, the polyurethane-based oligomer has a number average molecular weight of 10,000 to 20,000 g/mol.

Further, the block copolymer of the present invention is a multi-block copolymer such as a triblock copolymer or a pentablock copolymer.

Further, the block copolymer is selected from among compounds represented by Formulae below:

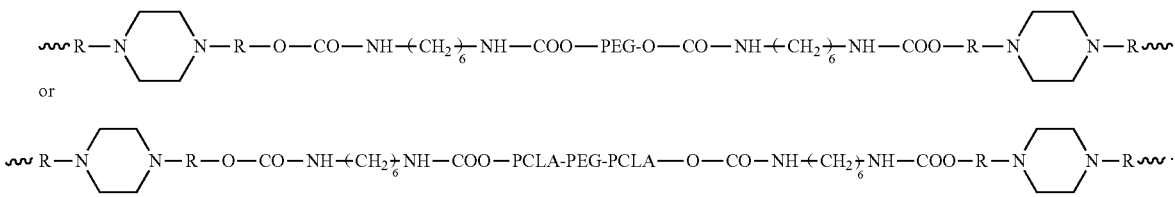

Further, the block copolymer has a molecular weight ratio of a hydrophobic block to a hydrophilic block of 1:1 to 1:3.

Further, the multiblock copolymer has a number average molecular weight of 14,000 to 30,000.

The present invention provides a method of preparing a temperature and pH-sensitive block copolymer having excellent gel strength, comprising: (a) synthesizing a poly(ethylene glycol)-based compound (A) or a copolymer (B) of the poly(ethylene glycol)-based compound (A) and a biodegradable polymer; and (b) coupling a polyurethane-based oligomer (C) with the compound (A) or the copolymer (B).

In the present invention, the method further comprises, after the synthesis of the compound (A) or the copolymer (B) introducing a hydroxy group into the copolymer (B).

Further, the synthesis of the copolymer (B) is conducted at a temperature of 130~150° C. for 12~48 hours.

Further, in the method, one or more catalysts selected from the group consisting of stannous octoate, stannous chloride, iron oxide, aluminum triisopropoxide, $CaH_2$, Zn, lithium chloride, and tris (2,6-di-tert-butylphenolate) may be used.

The present invention provides a method of preparing a temperature and pH-sensitive block copolymer having excellent gel strength, comprising: polymerizing poly(ethylene glycol) methyl ether with ε-caprolactone to form a polymer in a nitrogen atmosphere; dissolving the polymer in methylene chloride to remove unreacted reactants therefrom; dissolving the polymer from which the unreacted reactants are removed in chloroform and then reacting the polymer with 1,6-diisocyanate hexane and 1,4-bis(2-hydroxyethyl)piperazine or 1,3-bis{1-(2-hydroxyethyl)-4-pyridyl}propane (HEP) to form a polyurethane block; and dissolving the reaction product in excess ethylether to remove unreacted reactants therefrom.

The present invention provides a polymer hydrogel type drug delivery system, comprising:
  (a) the block copolymer prepared using the method; and
  (b) a physiologically active substance which can be included in the block copolymer.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
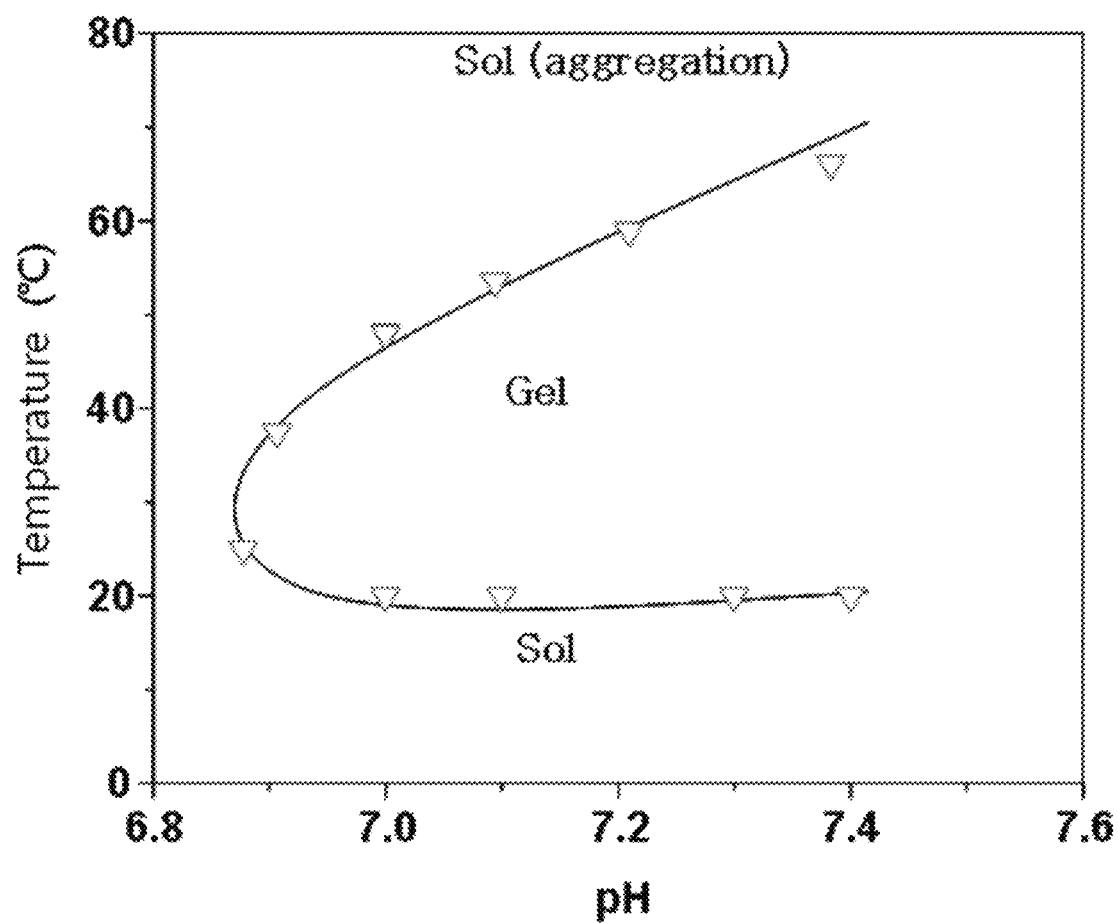
FIG. 1 is a graph showing the sol-gel transition behavior of a block copolymer depending on temperature and pH according to an embodiment of the present invention.

Hereinafter, preferred embodiments of the present invention will be described in detail with reference to the attached drawings. Reference now should be made to the drawings, in which the same reference numerals are used throughout the different drawings to designate the same or similar components. In the description of the present invention, the detailed description of commonly-known functions or constitutions related to the present invention will be omitted in order to make the essential points of the present invention clear.

The present invention provides a novel temperature- and pH-sensitive multiblock copolymer, which has excellent gel strength and is sensitive to pH as well as temperature by coupling a polyurethane-based oligomer, the ionization degree of which is changed depending on pH, with a poly (ethylene glycol)-based compound or a copolymer of the poly(ethylene glycol)-based compound and a biodegradable polymer, which is hydrophilic and is sensitive to temperature, a method of preparing the block copolymer, and a hydrogel type drug delivery system.

One of the components of the temperature and pH-sensitive block copolymer according to the present invention is a copolymer (B) of a poly(ethylene glycol)-based compound (A) and a biodegradable polymer. Since the copolymer (B) has both the hydrophilicity of the poly(ethylene glycol)-based compound (A) and the hydrophobicity of the biodegradable polymer, it can change from a sol state to a gel state depending on changes in temperature.

As the poly(ethylene glycol)-based compound constituting the copolymer (B), general poly(ethylene glycol)-based compounds well-known in the related field may be used without limitation, and, particularly, it is preferred that the poly(ethylene glycol)-based compound be represented by Formula 1 below:

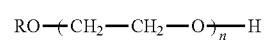

[Formula 1]

wherein R is hydrogen or an alkyl group of 1 to 5 carbon atoms, and n is a natural number ranging from 11 to 45.

The poly(ethylene glycol)-based compound may have a number average molecular weight (Mn) ranging from 1000 to 5000 g/mol, and particularly, poly(ethylene glycol) (PEG), represented by Formula 1 above, wherein R is hydrogen, may have a number average molecular weight ranging from 1000 to 2000 g/mol. Further, methoxy poly(ethylene glycol) (MPEG), represented by Formula 1 above, wherein R is a methyl group, may have a number average molecular weight ranging from 1000 to 5000 g/mol.

When the number average molecular weight of the poly (ethylene glycol)-based compound deviates from the above range, that is, when it is below 1000 g/mol or above 5000 g/mol, gel cannot be easily formed, and gel strength is decreased even if gel is formed, and thus it is difficult to apply it to a drug delivery system.

As the biodegradable polymer constituting the copolymer (B), general biodegradable polymers well known in the related field, and preferably biodegradable aliphatic polyester polymers, may be used. Examples of the biodegradable polymer may include polylactide (PLA), polyglycolide (PGA), polycaprolactone (PCL), poly(caprolactone-lactide) random copolymer (PCLA), poly(caprolactone-glycolide) random copolymer (PCGA), poly(lactide-glycolide) random copolymer (PLGA), and mixtures thereof.

It is preferred that the molecular weight ratio of the poly (ethylene glycol)-based compound to the biodegradable polymer in the copolymer (B) be in a range of 1:1 to 1:3, but the invention is not limited thereto. When the molecular weight ratio thereof is below 1:1, gel cannot be formed. Conversely, when the molecular weight ratio thereof is above 1:3, hydrophobicity is increased, and thus the prepared block copolymer cannot be dissolved in water.

Further, when the biodegradable polymer in the copolymer (B) is PCLA, PCGA or PLGA, the effect of the sensitivity to temperature and pH can be increased by properly adjusting the molar ratio thereof.

As the other of the components of the temperature and pH-sensitive block copolymer according to the present invention, compounds having various ionization degrees depending on pH may be used without limitation, and preferably a polyurethane-based oligomer (C), having both hydrophobicity and pH-sensitivity, may be used.

It is further preferred that the polyurethane-based oligomer include functional groups, such as a diisocyanate group (NCO—R—NCO), a diol group (HO—R'—OH) and the like, which can react with a temperature-sensitive block, in order to make it easy to prepare the block copolymer according to the present invention through a polymerization reaction. In particular, the polyurethane-based oligomer can exhibit pH-sensitivity in the body by using a diol group including a tertiary amine group ionized at a pH of 7.0 or less.

Here, the diisocyanate compound, represented by Formula 2 below, may be one or more selected from the group consisting of 1,2-diisocyanate ethane, 1,4-diisocyanate butane, 1,3-diisocyanate butane, 1,6-diisocyanate hexane, 1,7-diisocyanate heptane, 1,8-diisocyanate octane, 1,9-diisocyanate nonane, 1,10-diisocyanate decane, 1,12-diisocyanate decane, bis(4-isocyanatecycloethyl)methane, bis(4-isocyanatephenyl)methane, bis(4-isocyanatephenyl)ether, bis(4-isocyanatephenyl)sulfone, 4,4'-diphenylmethane diisocyanate, and hydrogenated 4,4'-diphenylmethane diisocyanate.

[Formula 2]

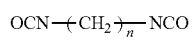

wherein n is an integer of 4 to 10.

Further, the diol compound may be one or more selected from the group consisting of 1,3-bis{1-(2-hydroxyethyl)-4-peridyl}propane, 1,4-bis(2-hydroxyethyl)piperazine, 1,4-bis(2-hydroxymethylphenyl)piperazine, and 1,4-bis-(2-hydroxyfluorophenyl)piperazine.

Meanwhile, the diol compound, comprising a tertiary amine on a main chain thereof as a pH sensitive component, is represented by Formula 3 below:

[Formula 3]

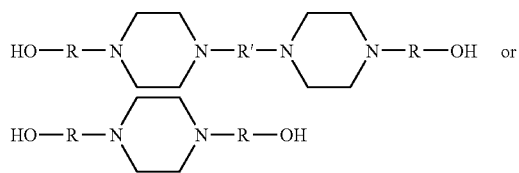

wherein R and R' are alkyl groups of 1 to 8 carbon atoms, respectively. Examples thereof may include 1,3-bis{1-(2-hydroxyethyl)-4-pyridyl}propane, 1,4-bis(2-hydroxyethyl)piperazine, 1,4-bis(2-hydroxymethylphenyl)piperazine, and 1,4-bis-(2-hydroxyfluorophenyl)piperazine, 1,4-bis(2-hydroxyethyl)piperazine mono-lactate, 1,4-bis(2-hydroxyethyl)piperazine di-lactate, 1,3-[1-2-hydroxyehtyl)-4-piperidyl]propane mono-lactate, 1,3-[1-(2-hydroxyehtyl)-4-piperidyl]propane di-lactate.

When the pH sensitive polyurethane-based oligomer is prepared, it is preferred that the molar ratio of the diisocyanate to the diol compound in the reaction be in the range of 1:1 to 1:3.

When the molar ratio of the diisocyanate to the diol is below 1:1 or above 1:3, pH sensitivity is decreased due to the wide distribution of polymers formed after polymerization, and it is difficult to adjust the block length of the block copolymer.

It is preferred that the number average molecular weight of the polyurethane-based oligomer be in the range from 10,000 to 20,000 g/mol, but the invention is not limited thereto. When the number average molecular weight of the polyurethane-based oligomer is below 10,000 g/mol, sol-gel transition behavior depending on the change in pH does not appear at a pH of about 7.0~7.4, and at a temperature of 37° C., which are the conditions in the body, and gel strength is decreased due to the low molecular weight. In contrast, when the number average molecular weight thereof is above 20,000 g/mol, it is difficult to exhibit both temperature sensitivity and pH sensitivity at a pH of about 7.0~7.4 and at a temperature of 37° C., which are the conditions in the body.

In a triblock or pentablock copolymer prepared by polymerizing the pH-sensitive polyurethane-based oligomer with the temperature-sensitive poly(ethylene glycol) or copolymer of the poly(ethylene glycol) and a biodegradable polymer at a proper ratio, the polyurethane-based oligomer has ionization characteristics such that the solubility of the oligomer in water differs depending on pH due to a tertiary amine group present in the oligomer itself, thus forming a hydrogel or maintaining the oligomer in a sol state depending on the change in pH.

The above compounds may be prepared using general methods commonly known in the related art. For example, a temperature and pH-sensitive block copolymer hydrogel can be prepared by polymerizing a compound having isocyanate groups on both ends thereof with a temperature-sensitive polymer block having hydroxyl groups on both ends thereof through a urethane reaction to form a polymer and then reacting the polymer with a diol group having a tertiary amine group, which is a pH-sensitive component, at a proper ratio.

The block copolymer of the present invention, formed by coupling a copolymer (B) of the poly(ethylene glycol)-based compound (A) and a biodegradable polymer with a polyurethane-based oligomer (C), may be a multiblock copolymer, preferably a triblock or pentablock copolymer, and may be represented by Formulae 4 to 6 below:

[Formula 4]

[Formula 5]

[Formula 6]

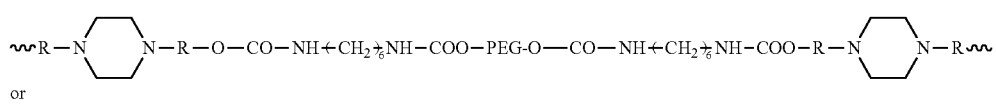

or

The triblock or pentablock copolymer, represented by Formulae 4 to 6, can be formed into a hydrogel or can change from a sol state to a gel state depending on the change in pH because it includes a hydrophilic poly(ethylene glycol) block, a hydrophobic biodegradable polymer block, and a pH-sensitive and hydrophobic polyurethane oligomer block. In particular, the triblock or pentablock copolymer can yield satisfactory results in applications requiring pH sensitivity, for example, drug delivery systems for discharging drugs, diagnosis, etc.

In this case, the poly(ethylene glycol) (HO-PEG-OH) or the triblock copolymer of the poly(ethylene glycol) and a biodegradable polymer, represented by Formula 5 above, can react with a diisocyanate group(OCN—R'—NCO) and then can have a block structure coupled with polyurethane oligomers at both sides thereof because the copolymer (HO-PLCA-PEG-PCLA-OH) of the poly(ethylene glycol)-based compound and a biodegradable polyester polymer has hydroxy groups at both ends thereof.

The triblock or pentablock copolymer may have a number average molecular weight of 14,000 to 30,000 g/mol. Here, in order to prepare a temperature-sensitive block copolymer, a biodegradable polyester polymer having a molecular weight of 3,000 to 5,000 g/mol and a poly(ethylene glycol)-based compound having a molecular weight of 1000 to 5,000 g/mol are used such that the block copolymer has a molecular weight ratio of a hydrophobic block to a hydrophilic block of 1:1 to 1:3. When the molecular weight ratio thereof is below 1:1, gel is not formed. In contrast, when the molecular weight thereof is above 1:3, hydrophobicity is increased, and thus the block copolymer is not dissolved in water.

The temperature and pH-sensitive block copolymer according to the present invention may include commonly-used additives and other components in addition to the above components.

In order to prepare the temperature and pH-sensitive block copolymer according to the present invention using a copolymer (B) of the poly(ethylene glycol)-based compound (A) and the biodegradable polymer and a polyurethane-based oligomer (C), any one of various polymerization methods, such as radical polymerization, cationic polymerization, anionic polymerization, condensation polymerization, and the like, which are well known in the art, may be used.

Meanwhile, a method of preparing a temperature and pH-sensitive block copolymer according to an embodiment of the present invention may include: (a) polymerizing a poly(ethylene glycol)-based compound (A) with a biodegradable polymer to prepare a copolymer (B); (b) introducing a hydroxy group into the copolymer (B); and (c) coupling a polyurethane-based oligomer (C), having a diisocyanate group and a diol group, with the copolymer (B).

First, the reaction of polymerizing a poly(ethylene glycol)-based compound (A) with a biodegradable polyester polymer to prepare a copolymer (B) may be represented by Equation 1 below.

[Equation 1]

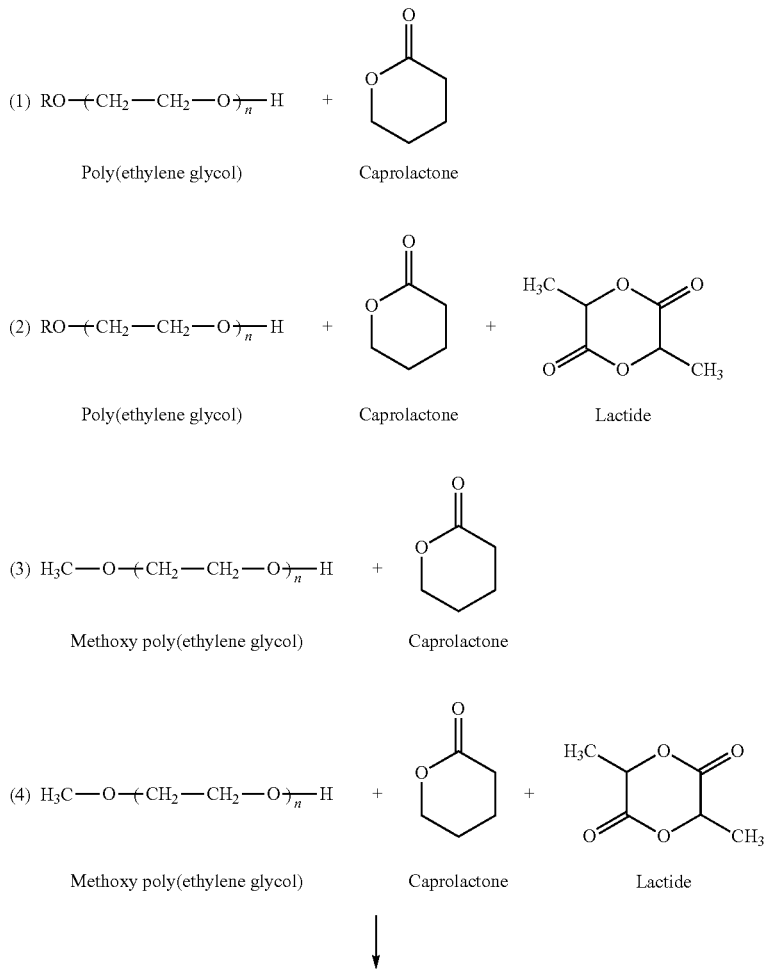

(1) 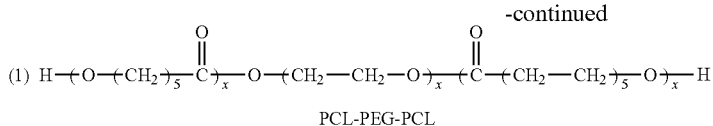
PCL-PEG-PCL (2) 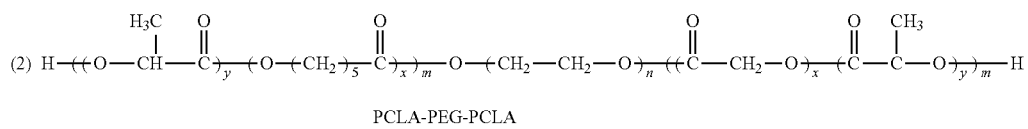
PCLA-PEG-PCLA (3) 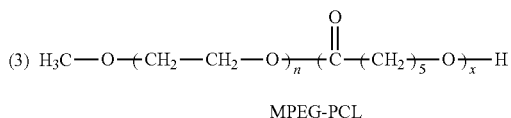
MPEG-PCL (4) 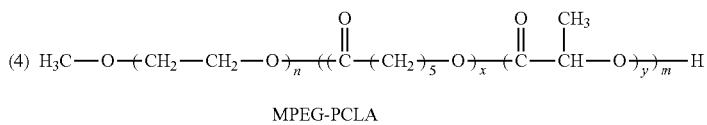
MPEG-PCLA The copolymerization of the poly(ethylene glycol)-based compound and the biodegradable polyester polymer may be conducted using ring-opening polymerization. In this case, the copolymerization thereof may be conducted at a temperature of 130~150° C. for 12~48 hours, but is not limited thereto. Further, catalysts may be used in order to impart reactivity to the copolymerization thereof. Examples of catalysts that may be used include stannous octoate, stannous chloride, iron oxide, $GeO_2$, $Sb_3O_2$, $SnO_2$, aluminum triisopropoxide, $CaH_2$, Zn, lithium chloride, tris(2,6-di-tert-butylphenolate), and the like. Furthermore, the molecular weight and kind of the above biodegradable polymer may be adjusted in order to vary the degree of hydrophobicity.

In the process of introducing a diisocyanate group into a triblock copolymer of polycaprolactone-b-polylactic acid-polyethylene-b-polylactic acid-polycaprolactone, formed through the ring-opening polymerization of the poly(ethylene glycol)-based oligomer and the biodegradable polymer, it is preferred that the diisocyanate group be introduced into a hydroxy group (—OH) placed at the end of a copolymer of poly(ethylene glycol) and biodegradable polyester through a urethane reaction of diisocyanate. This reaction may be represented by Equation 2 below.

[Equation 2]

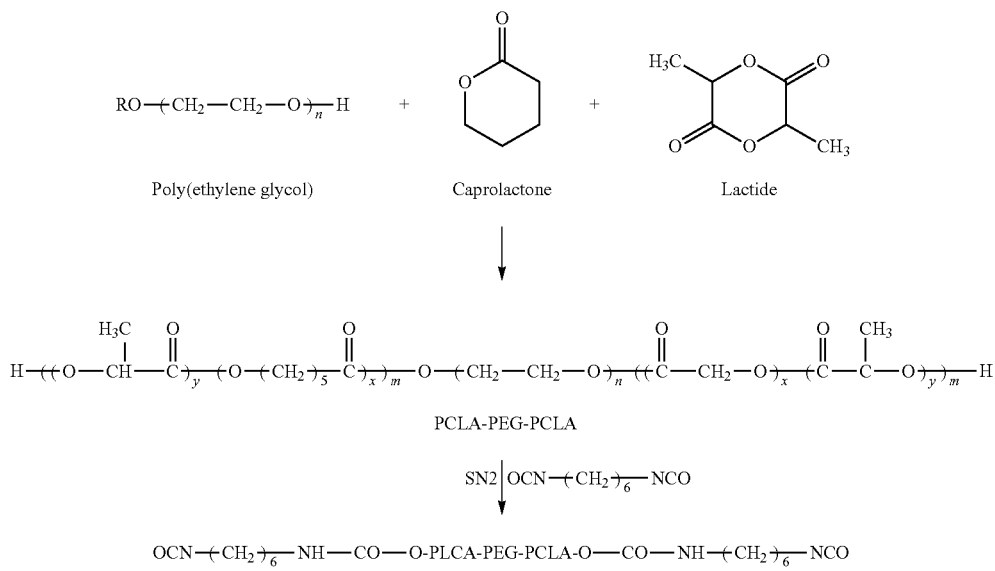

The copolymer (B) of a poly(ethylene glycol)-based compound and biodegradable polyester polymer may be formed into a temperature and pH-sensitive pentablock copolymer according to the present invention through a urethane reaction of a diol group (HO—R—OH) and a diisocyanate group (OCN—R—NCO). This reaction may be represented by Equation 3 below.

The present invention provides a polymer hydrogel type drug delivery system, including: (a) the temperature and pH-sensitive block copolymer; and (b) a physiologically active substance which can be included in the block copolymer.

The physiologically active substance which can be included in the polymer hydrogel type block copolymer may be used without limitation, and examples of the physiologi-

[Equation 3]

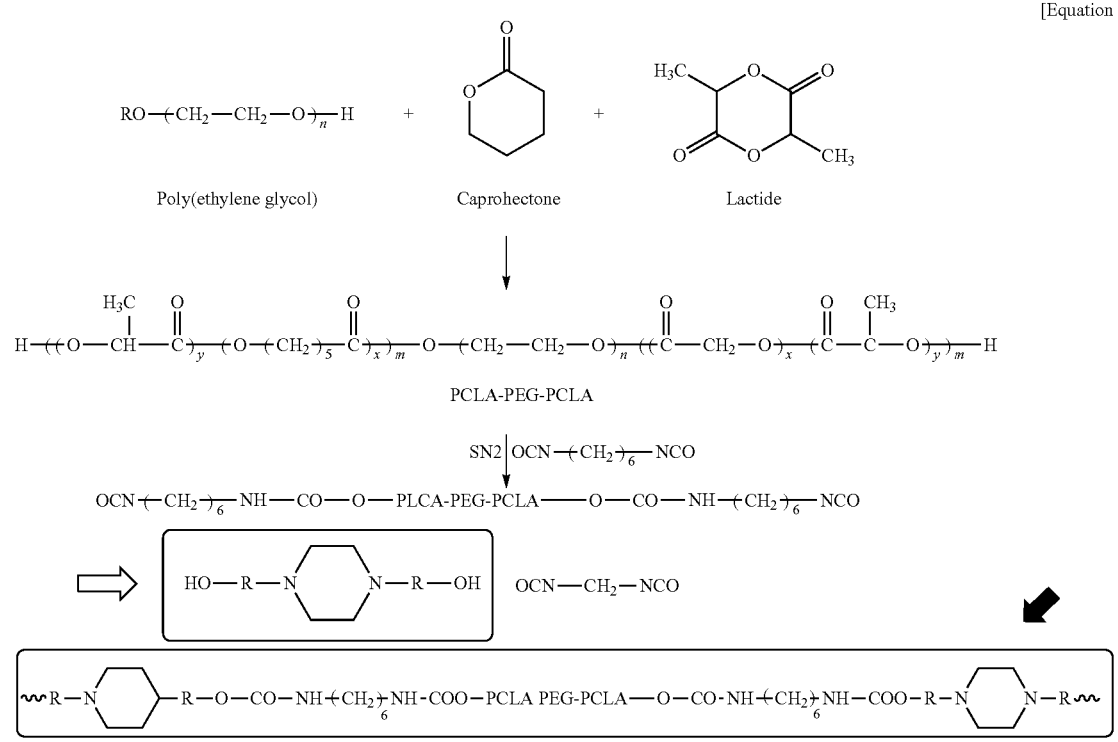

In this process, the reaction temperature and time are not particularly limited.

The diisocyanate compound used to prepare the polyurethane-based oligomer and the diol compound including tertiary amine are described above. Since the multiblock copolymer prepared using the above methods, as described above, has a structure in which a hydrophilic block, a hydrophobic block, and a polyurethane-base oligomer, which can exhibit various ionization degrees depending on the change in pH, are combined with each other, the multiblock copolymer can exhibit both temperature sensitivity and pH sensitivity.

In practice, in the poly(ethylene glycol)-polycaprolactone-polylactide-polyurethane (PU-PCLA-PEG-PCLA-PU) block copolymer, prepared using the above methods, the introduction of functional groups thereinto and the reaction between end groups thereof were observed using FT-IR and $^1$H-NMR. Further, it was found that the PU-PCLA-PEG-PCLA-PU block copolymer has a structure in which a copolymer of a poly(ethylene glycol)-based compound and a biodegradable polymer is coupled with a polyurethane-based oligomer through the increase in molecular weight of the block copolymer using gel permeation chromatography (GPC). Furthermore, in order to evaluate pH sensitivity, the change in the sol-gel transition characteristics was measured while changing pH depending on temperature, and thus it was found that the multiblock copolymer of the present invention has pH sensitivity characteristics.

cally active substance may include protein drugs, such as insulin, exendin-4, human growth hormone (HGH), erythropoietin (EPO), granulocyte colony stimulating factor (G-CSF), granulocyte-macrophage stimulating factor (GM-CSF) and the like; and medical drugs, such as anticancer drugs, antibacterial drugs, steroids, anti-inflammatory drugs, sex hormones, immunosuppression drugs, antiviral drugs, anesthetic drugs, antinauseants, antihistamines and the like. Other examples of the physiologically active substance may include commonly-known additives, such as excipients, stabilizing agents, pH adjusters, antioxidants, preservatives, binders, disintegrators, and the like. In this case, the drug delivery system may additionally include additives, solvents, and the like, which are commonly known in the art.

Further, the polymer hydrogel type drug delivery system may be used in the form of an oral agent or a parenteral agent, and may be formed into an intravenous, intramuscular or hypodermic injection.

Additionally, the present invention provides a method of using the temperature and pH-sensitive block copolymer as a carrier for delivering drugs or diagnosing diseases. In this case, the substances included in the block copolymer are not limited as long as they are used to cure, prevent and diagnose diseases.

Hereinafter, the present invention will be described in more detail with reference to the following Examples. However, the following Examples are set forth to illustrate the present invention, but are not to be construed as the limit of the present invention.

EXAMPLES 1 TO 3

Synthesis of Temperature and pH-Sensitive Triblock Copolymer

Example 1

Preparation of poly(caprolactone-b-lactic acid)-poly (ethylene glycol)-poly(caprolactone-b-lactic acid) triblock copolymer (PCLA-PEG-PCLA)

10 g of poly(ethylene glycol) methyl ether (PEG 1,500, Mn=1,500) and 0.2 g of stannous octoate, which is a catalyst, were put into a reactor, and were then dried in a vacuum at a temperature of 110° C. for 4 hours in order to remove moisture therefrom. Subsequently, the dried reactants were cooled, and then 6.0 g of ε-caprolactone (5.576 ml) and 1.43 g of D,L-lactide, which are biodegradable polyester polymer compounds, were added to the dried reactant in a nitrogen atmosphere to form a reaction mixture. Then, the reaction mixture was slowly heated to a temperature of 135° C. in a nitrogen atmosphere and then polymerized for 24 hours to form a reaction product. After the polymerization reaction, the reaction product was cooled to room temperature, and was then dissolved by adding a small amount of methylene chloride thereto. The dissolved reaction product was added to excess ethyl ether and then precipitated to remove unreacted materials therefrom. Then, the reaction product, from which unreacted material was removed, was dried in a vacuum at a temperature of 40° C. for 48 hours, thereby obtaining a triblock copolymer (PCLA-PEG-PCLA) in which hydroxy groups are provided at the ends of the formed poly(ethylene glycol) and biodegradable polyester polymer compound, ε-caprolactone and lactic acid. The yield of the triblock copolymer thus obtained was 91%.

Example 2

A triblock copolymer (PCLA-PEG-PCLA) having a molecular weight of 7500 was prepared using the same method as in Example 1, except that the molar ratio of the biodegradable polymer, that is, the molar ratio of ε-caprolactone to D,L-lactide, is 1/2.

Example 3

A triblock copolymer (PCLA-PEG-PCLA) having a molecular weight of 8000 was prepared using the same method as in Example 1, except that the molar ratio of the biodegradable polymer, that is, the molar ratio of ε-caprolactone to D,L-lactide, is 1/3.

EXAMPLES 4 TO 6

Synthesis of Temperature and pH-Sensitive Pentablock Copolymer

Example 4

4 g of poly(ethylene glycol) methyl ether (PEG 2,000, Mn=2,000) and 0.02 g of stannous octoate, which is a catalyst, were put into a reactor, and were then dried in a vacuum at a temperature of 110° C. for 4 hours in order to remove moisture therefrom. Subsequently, the dried reactants were cooled, and then 4.97 g of ε-caprolactone (4.61 ml), which is a biodegradable polyester polymer compound, was added to the dried reactant in a nitrogen atmosphere and then dried in a vacuum at a temperature of 65° C. for 1 hour. Thereafter, the dried reactants were cooled to room temperature, and then 1.43 g of D,L-lactide was added to the dried reactants and then cooled in a vacuum at a temperature of 85° C. for 1 hour to form a reaction mixture. Then, the reaction mixture was slowly heated to a temperature of 135° C. in a nitrogen atmosphere and then polymerized for 24 hours to form a reaction product. After the polymerization reaction, the reaction product was cooled to room temperature, and was then dissolved by adding a small amount of methylene chloride thereto. The dissolved reaction product was added to excess ethyl ether and then precipitated to remove unreacted materials therefrom. Then, the reaction product, from which unreacted material was removed, was dried in a vacuum at a temperature of 40° C. for 48 hours, thereby obtaining a triblock copolymer (PCLA-PEG-PCLA) of the formed poly(ethylene glycol) and biodegradable polyester polymer compound, ε-caprolactone and lactic acid. The yield of the triblock copolymer thus obtained was 91%.

Meanwhile, the obtained triblock copolymer (PCLA-PEG-PCLA) having hydroxy groups was put into a reactor, and was then dissolved by adding chloroform thereto. Meanwhile, in order to form a polyurethane block, 1,6-diisocyanate hexane and 1,4-bis(2-hydroxyethyl)piperazine were added, dissolved, and then reacted with the triblock copolymer (PCLA-PEG-PCLA) having hydroxy groups such that the molar ratio of the triblock copolymer, 1,6-diisocyanate hexane and 1,4-bis(2-hydroxyethyl)piperazine was 1:2.8:3. After the reaction, the reaction product was precipitated in excess ethyl ether to remove unreacted materials therefrom, and was then filtered, thereby preparing a pentablock copolymer (PU-PCLA-PEG-PCLA-PU) having a molecular weight of 27500. The yield of the obtained pentablock copolymer was 80% or more.

Example 5

A pentablock copolymer (PU-PCLA-PEG-PCLA-PU) having a molecular weight of 25550 was prepared using the same method as in Example 4, except that the molar ratio of the triblock copolymer having hydroxy groups, 1,6-diisocyanate hexane and 1,4-bis(2-hydroxyethyl)piperazine was 1:2.5:3.

Example 6

A pentablock copolymer (PU-PCLA-PEG-PCLA-PU) having a molecular weight of 25550 was prepared using the same method as in Example 4, except that the molar ratio of the triblock copolymer (PCLA-PEG-PCLA) having hydroxy groups, 1,6-diisocyanate hexane and 1,4-bis(2-hydroxyethyl) piperazine was 1:3:4.

Example 7

A pentablock copolymer (PU-PCLA-PEG-PCLA-PU) having a molecular weight of 27,550 g/mol was prepared using the same method as in Example 4, except that the diol, which is a component of a polyurethane-based oligomer, was 1,3-bis{1-(2-hydroxyethyl)-4-pyridyl}propane (HEP).

Experimental Example 1

Evaluation of Sol-Gel Transition Behavior Depending on pH Change

The sol-gel transition behavior of the block copolymer prepared according to the present invention depending on the change in temperature and pH was evaluated.

30 wt % of the triblock copolymer (PCLA-PEG-PCLA) prepared in Example 1 and the pentablock copolymer (PU-PCLA-PEG-PCLA-PU) prepared in Example 4 were added and dissolved in a buffer solution, and were then titrated at 50° C. using a sodium hydroxide (NaOH) solution, and thus the pH was adjusted to 5.5, 6.0, 6.5, 7.0, and 7.5, respectively. Subsequently, the triblock copolymer solution having the respective pH was left in equilibrium at constant temperature for 10 minutes after heating the triblock copolymer solution by 2° C., and was then tilted, and thus the sol-gel transition behavior of the triblock copolymer was measured.

FIG. 1 is a graph showing the sol-gel transition behavior of a block copolymer depending on temperature and pH according to an embodiment of the present invention.

More specifically, FIG. 1 is a graph showing the sol-gel transition behavior of the pentablock copolymer including a temperature-sensitive poly(ethylene glycol)-based compound, a biodegradable compound of polycaprolactone and polylactic acid, and a biodegradable pH-sensitive polyurethane-based oligomer compound, prepared in Example 4, depending on temperature and pH.

As shown in FIG. 1, it can be seen that the sol-gel transition behavior of the block copolymer of the present invention was reversibly conducted depending on the change in temperature and pH because the ionization degree of the polyurethane-based oligomer in the block copolymer changed depending on the change in pH, and the hydrophobicity of the biodegradable polymer compound in the block copolymer changed depending on the change in temperature.

Figure 2:
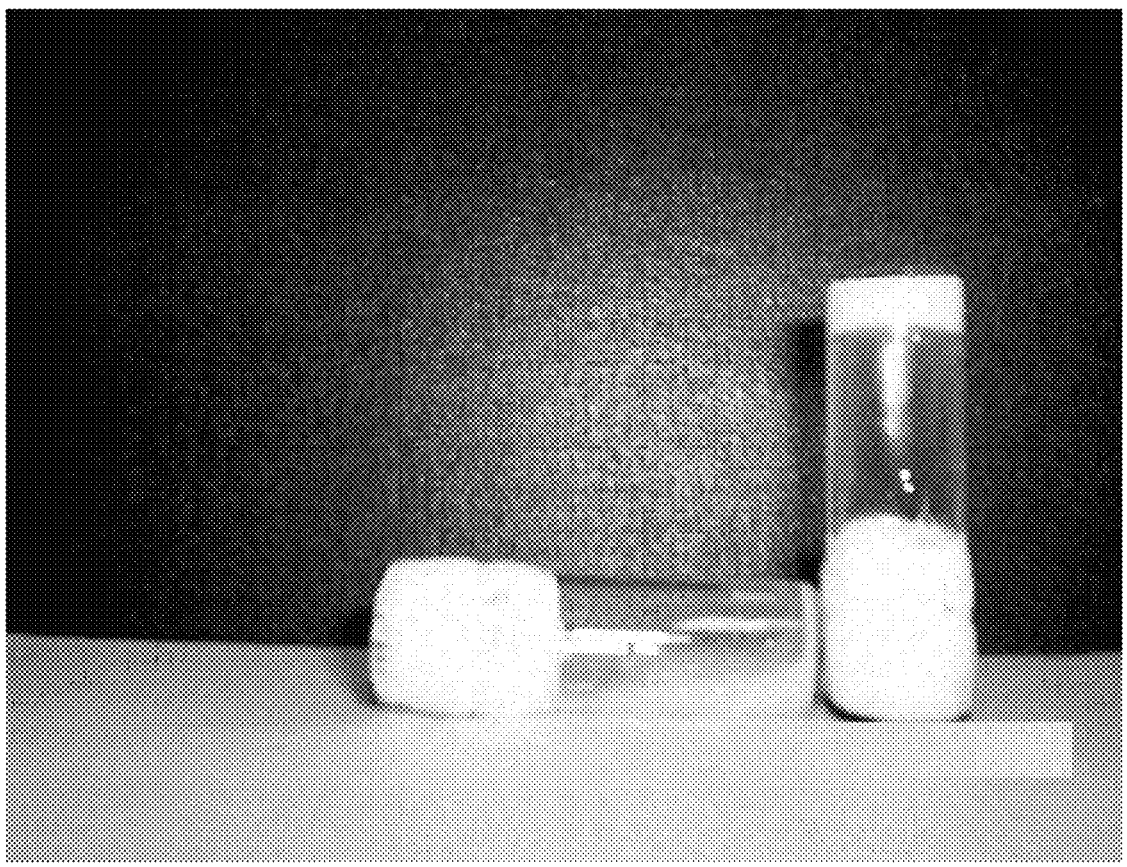
FIG. 2 is a photograph showing the sol-gel transition behavior of a 30% solution of a pentablock copolymer, comprising a poly(ethylene glycol)-based compound, polycaprolactone, a polylactic acid compound and a polyurethane-based oligomer compound, at a temperature of 37° C. depending on pH according to an embodiment of the present invention.
Figure 3:
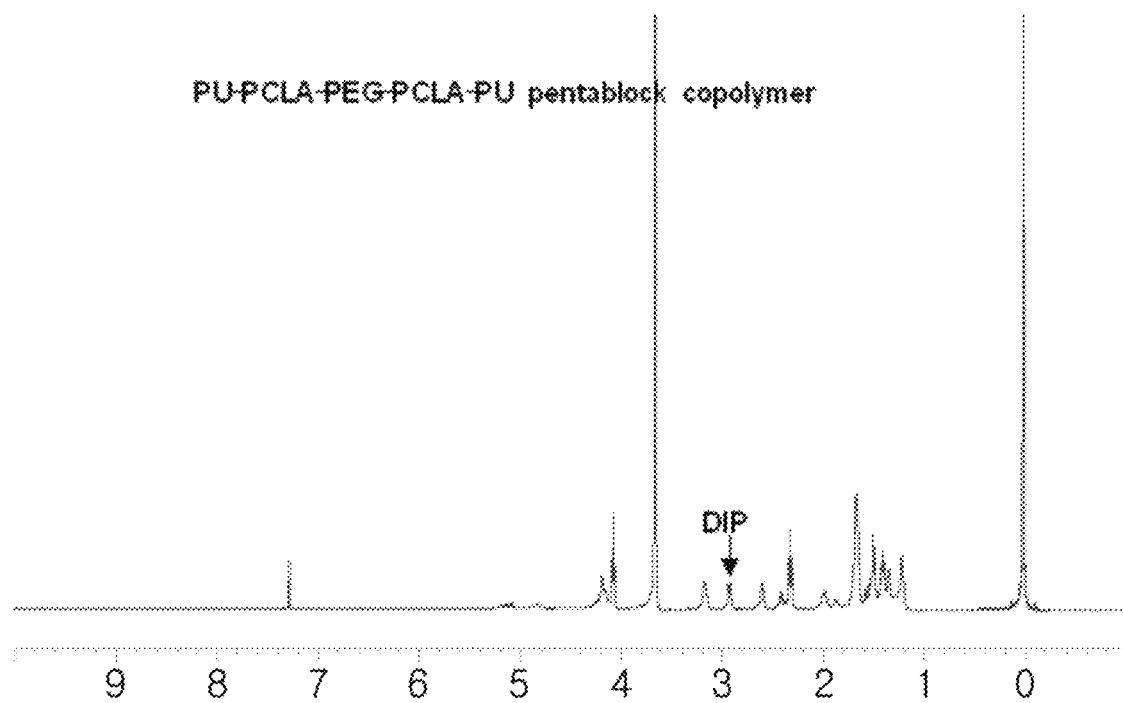
FIG. 3 is an NMR graph of a pentablock copolymer, prepared in Example 6, comprising a poly(ethylene glycol)-based compound, polycaprolactone, a polylactic acid compound and a polyurethane-based oligomer compound, at a temperature of 37° C. depending on pH according to an embodiment of the present invention.
Figure 4:
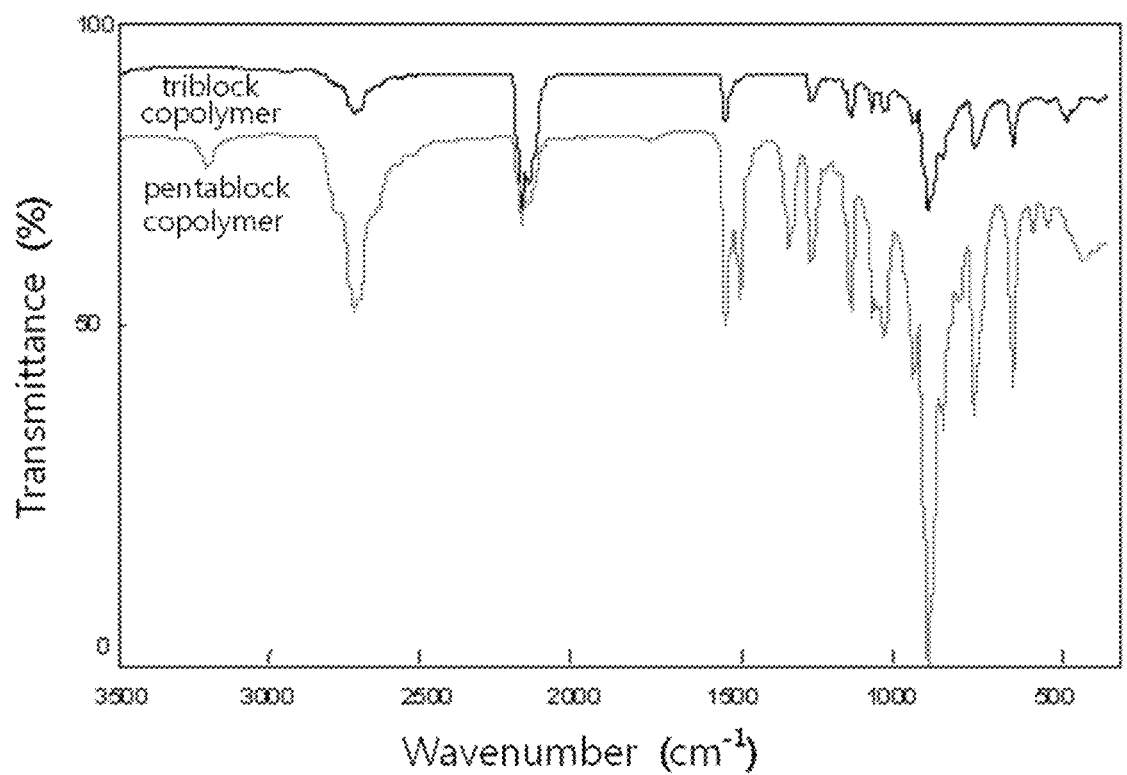
FIG. 4 is an IR graph of a triblock copolymer and a pentablock copolymer, prepared in Examples 1 and 6.

As shown in FIG. 2, it was found that, since the prepared hydrogel type block copolymer exhibits sol-gel transition characteristic at a specific pH, the block copolymer is gelated at a pH ranging from 7.0 to 7.4, which is similar to that in the body, and is solated outside that pH range, so that an injection needle is not clogged at the time of injecting the block copolymer into the body, thereby safely forming gel in the body, whereas the injection needle is clogged at the time of injecting the conventional temperature-sensitive hydrogel into the body. Therefore, it was also found that the prepared block copolymer can be applied to a carrier for discharging drugs targeted at a specific temperature and pH. Meanwhile, since the polyurethane-based oligomer having excellent gel strength is used as a pH-sensitive of the block copolymer, the block copolymer can be suitably used as a drug delivery system for discharging drugs for a relatively long time.

Experimental Example

Evaluation of Gel Strength

The gel strength of the block copolymer prepared according to the present invention was evaluated after the sol-gel transition thereof, depending on the change in temperature and pH.

30 wt % of the triblock copolymer (PCLA-PEG-PCLA) prepared in Example 1 and the pentablock copolymers (PU-PCLA-PEG-PCLA-PU) prepared in Examples 4, 5 and 7 were added and dissolved in a buffer solution, and were then titrated using a sodium hydroxide (NaOH) solution at a temperature of 50° C., and thus the pH was adjusted to 7.4. Subsequently, the sol-gel transition thereof was completely conducted, and thus the block copolymer solutions were in equilibrium, and then the gel strength of the hydrogel was measured.

Figure 5:
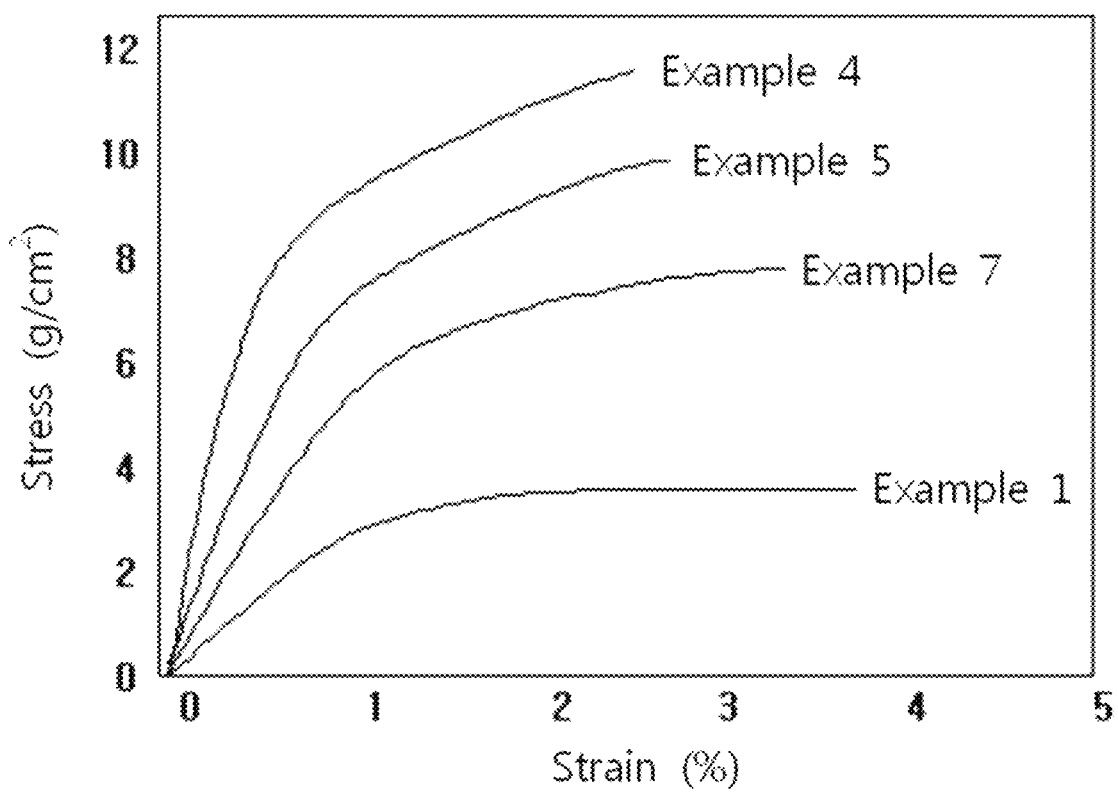
FIG. 5 is a graph showing the gel strengths of a triblock copolymer and a pentablock copolymer, prepared in Examples 1 to 6, comprising a poly(ethylene glycol)-based compound, polycaprolactone, a polylactic acid compound and a polyurethane-based oligomer compound.

FIG. 5 is a graph showing the gel strength of the hydrogel completely gelated at a temperature of 37° C. and a pH of 7.4.

Since the temperature and pH-sensitive block copolymer of the present invention forms a stable hydrogel at a specific pH, for example, at a pH of 7.0 to 7.4, which is the pH range of normal cells in the body, and maintains a sol state at a pH of 6.0 to 7.0, which is the pH range of abnormal cells, such as cancer cells, in the body, it can be used as a carrier for discharging drugs targeted to cancer cells. That is, the block copolymer cannot form a hydrogel at low pH (below 7.0) because the ionization degree of the tertiary amine present in the polyurethane-based oligomer is increased, and thus all of the polyurethane becomes water-soluble, and exhibits hydrophobic characteristics at a pH of 7.0 or more because the ionization degree of the polyurethane is decreased.

Accordingly, the multiblock copolymer of the present invention can exhibit sol-gel transition characteristics sensitive to pH as well as temperature.

The block copolymer according to the present invention is advantageous in that both temperature sensitivity and pH sensitivity are imparted thereto by coupling a polyurethane-based oligomer, which exhibits various ionization degrees depending on the change in pH, with a block copolymer including a hydrophilic polymer and a biodegradable polymer, and in that the above mentioned problem with the temperature-sensitive hydrogel can be overcome.

Further, the block copolymer according to the present invention is advantageous in that, since it has excellent gel strength at the time of injecting it into the body and is early biodegraded, it can be formed into a stable hydrogel which can prevent drugs from being excessively discharged early.

Further, the temperature and pH-sensitive block copolymer according to the present invention is advantageous in that it can be applied in the fields of gene delivery and drug delivery, and particularly can be applied as a drug delivery system for containing and discharging drugs because it is safe in the body, and it can also be applied to diagnostic imaging because it transfers materials for diagnosing diseases to abnormal cells.

Furthermore, the block copolymer according to the present invention is advantageous in that, since it forms a stable hydrogel at a pH of 7.0 to 7.4, which is a pH range of normal cells in the body, and maintains sol state at a pH of 7.0 or less, which is a pH range of abnormal cells, such as cancer cells, in the body, it can be used as a carrier for discharging drugs targeted to cancer cells, and additionally in that it can be usefully applied to genetic variation and other applications as well as cancer cells by properly adjusting the composition, molar ratio, molecular weight and/or functional group of the block copolymer.

As described above, although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An amphiphilic pentablock copolymer that is temperature- and pH-sensitive and has superior gel strength, comprising:
    (a) a hydrophilic triblock copolymer that is temperature-sensitive and that is a copolymer of a poly(ethylene glycol)-based compound (PEG) and a biodegradable polymer that is one or more polymer selected from the group consisting of polylactide (PLA), polyglycolide (PGA), polycaprolactone (PCL), poly(caprolactone-lactide) random copolymer (PCLA), poly(caprolactone-glycolide) random copolymer (PCGA), poly(lactide-glycolide) random copolymer (PLGA), and mixtures thereof; coupled with
    (b) a polyurethane-based oligomer (PU) that is pH sensitive and that comprises a diisocyanate compound polymerized with a diol compound,
    wherein the diisocyanate compound is represented by a Formula as follows:

OCN—(CH$_2$)$_n$—NCO, where n is an integer of 4 to 10, and
    wherein the diol compound has a tertiary amine on a main chain thereof, is one or more compound selected from the group consisting of 1,3-bis{1-(2-hydroxyethyl)-4-pyridyl}propane and 1,4-bis(2-hydroxyethyl)piperazine.

2. The amphiphilic pentablock copolymer according to claim 1, wherein the poly(ethylene glycol)-based compound is represented by a Formula as follows:

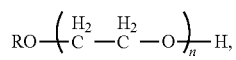

wherein R is hydrogen or an alkyl group of 1 to 5 carbon atoms, and n is a natural number ranging from 11 to 45.

3. The amphiphilic pentablock copolymer according to claim 1, wherein the poly(ethylene glycol)-based compound is a poly(ethylene glycol)(PEG)-based compound having a number average molecular weight ranging from 1000 to 5000 g/mol.

4. The amphiphilic pentablock copolymer according to claim 1, wherein the biodegradable polymer is a biodegradable aliphatic polyester.

5. The amphiphilic pentablock copolymer according to claim 1, wherein the copolymer has a molecular weight ratio of the poly(ethylene glycol)-based compound to the biodegradable polymer that ranges from 1:1 to 1:3.

6. The amphiphilic pentablock copolymer according to claim 1, wherein the diisocyanate compound is one or more compound selected from the group consisting of 1,4-diisocyanate butane, 1,6-diisocyanate hexane, 1,7diisocyanate heptane, 1,8-diisocyanate octane, 1,9-diisocyanate nonane, and 1,10-diisocyanate decane.

7. The amphiphilic pentablock copolymer according to claim 1, wherein the polyurethane-based oligomer has a molar ratio of the diisocyanate to the diol ranging from 1:1 to 1:3.

8. The amphiphilic pentablock copolymer according to claim 1, wherein the polyurethane-based oligomer has a number average molecular weight of 10,000 to 20,000 g/mol.

9. The amphiphilic pentablock copolymer according to claim 1, wherein the amphiphilic pentalock copolymer is selected from among compounds represented by Formulae as follows:

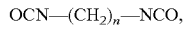
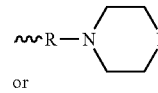
or
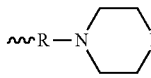
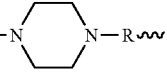
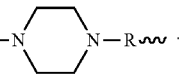

10. The amphiphilic pentablock copolymer according to claim 1, wherein the amphiphilic pentablock copolymer includes a hydrophobic block and a hydrophilic block, and has a molecular weight ratio of the hydrophobic block to the hydrophilic block ranging from 1:1 to 1:3.

11. The amphiphilic pentablock copolymer according to claim 1, wherein the amphiphilic pentablock copolymer has a number average molecular weight ranging from 14,000 to 30,000.

12. The amphiphilic pentablock copolymer according to claim 3, wherein the poly(ethylene glycol)-based compound is poly(ethylene glycol) (PEG)- based compound having a number average molecular weight ranging from 1000 to 2000 g/mol.

* * * * *